US008298189B2

(12) United States Patent
Fisher et al.

(10) Patent No.: US 8,298,189 B2
(45) Date of Patent: Oct. 30, 2012

(54) HEMOSTASIS VALVE

(75) Inventors: Mark S. Fisher, Sellersville, PA (US); W. Shaun Wall, North Wales, PA (US)

(73) Assignee: Medical Components, Inc., Harleysville, PA (US)

( * ) Notice: Subject to any disclaimer, the term of this patent is extended or adjusted under 35 U.S.C. 154(b) by 52 days.

(21) Appl. No.: 12/754,112

(22) Filed: Apr. 5, 2010

(65) Prior Publication Data

US 2010/0234807 A1  Sep. 16, 2010

Related U.S. Application Data

(62) Division of application No. 12/144,297, filed on Jun. 23, 2008, now Pat. No. 7,744,571.

(51) Int. Cl.
*A61M 5/178* (2006.01)

(52) U.S. Cl. .................................. 604/167.04

(58) Field of Classification Search .............. 604/167.04
See application file for complete search history.

(56) References Cited

U.S. PATENT DOCUMENTS

| 4,411,654 | A | 10/1983 | Boarini et al. |
| 4,436,519 | A | 3/1984 | O'Neill |
| 4,596,559 | A | 6/1986 | Fleischhacker |
| 4,610,665 | A | 9/1986 | Matsumoto |
| 4,655,752 | A | 4/1987 | Honkanen et al. |
| 4,747,833 | A | 5/1988 | Kousai et al. |
| 4,772,266 | A | 9/1988 | Groshong |
| 4,865,593 | A | 9/1989 | Ogawa et al. |
| 4,929,235 | A | 5/1990 | Merry et al. |
| 4,932,633 | A | 6/1990 | Johnson et al. |
| 4,983,168 | A | 1/1991 | Moorehead |
| 5,064,414 | A | 11/1991 | Revane |
| 5,085,645 | A | 2/1992 | Purdy et al. |
| 5,098,392 | A | 3/1992 | Fleischhacker et al. |

(Continued)

FOREIGN PATENT DOCUMENTS

EP  0631793 A1  1/1995
(Continued)

OTHER PUBLICATIONS

International Search Report (corrected), dated Mar. 26, 2009; PCT/US2008/067631 (6 pages).

(Continued)

*Primary Examiner* — Nicholas Lucchesi
*Assistant Examiner* — Jason Flick
(74) *Attorney, Agent, or Firm* — Glenn M. Massina; Fox Rothschild LLP

(57) ABSTRACT

A tearaway sheath assembly (100) having a splittable sheath tube (102) a splittable hub (110), a splittable valve (150) and a split cap (180). The valve (150) is of the elongated duckbill type and having a slit (158) almost completely across the distal end wall (154) such that two diverging sides (156) of the distal valve portion may be moved apart during insertion therethrough of a dilator or a catheter. A two-part cap (180) is affixed to the hub proximal end (120) and traps a seating flange (168) of the valve between itself and a seating groove (136) of the hub. Pairs of opposed gaps (184,122) of the cap (180) and the hub (110) are aligned with frangible sections or seams (108) of the sheath tube (102) and frangible sections (172) and slits (166) of the valve, facilitating splitting of the assembly (100) when desired by the practitioner to peel it away from the inserted catheter.

8 Claims, 8 Drawing Sheets

U.S. PATENT DOCUMENTS

| | | | |
|---|---|---|---|
| 5,125,904 | A | 6/1992 | Lee |
| 5,154,701 | A | 10/1992 | Cheer et al. |
| 5,167,634 | A | 12/1992 | Corrigan, Jr. et al. |
| 5,207,649 | A | 5/1993 | Aruny |
| 5,221,263 | A | 6/1993 | Sinko et al. |
| 5,250,033 | A | 10/1993 | Evans et al. |
| 5,269,771 | A | 12/1993 | Thomas et al. |
| 5,304,142 | A | 4/1994 | Liebl et al. |
| 5,312,355 | A | 5/1994 | Lee |
| 5,350,363 | A | 9/1994 | Goode et al. |
| 5,397,311 | A | 3/1995 | Walker et al. |
| 5,411,483 | A | 5/1995 | Loomas et al. |
| 5,423,762 | A | 6/1995 | Hillstead |
| 5,441,504 | A | 8/1995 | Pohndorf et al. |
| 5,456,284 | A | 10/1995 | Ryan et al. |
| 5,458,640 | A | 10/1995 | Gerrone |
| 5,613,953 | A | 3/1997 | Pohndorf |
| 5,720,759 | A | 2/1998 | Green et al. |
| 5,755,693 | A | 5/1998 | Walker et al. |
| 5,782,807 | A | 7/1998 | Falvai et al. |
| 5,885,217 | A | 3/1999 | Gisselberg et al. |
| 5,911,710 | A | 6/1999 | Barry et al. |
| 6,024,729 | A | 2/2000 | Dehdashtian et al. |
| 6,080,174 | A | 6/2000 | Dubrul et al. |
| 6,083,207 | A | 7/2000 | Heck |
| 6,197,016 | B1 | 3/2001 | Fourkas et al. |
| 6,277,100 | B1 | 8/2001 | Raulerson et al. |
| D450,839 | S | 11/2001 | Junker |
| 6,322,541 | B2 | 11/2001 | West et al. |
| 6,336,914 | B1 | 1/2002 | Gillespie, III |
| 6,454,744 | B1 | 9/2002 | Spohn et al. |
| 6,488,674 | B2 | 12/2002 | Becker et al. |
| 6,562,049 | B1 | 5/2003 | Norlander et al. |
| 6,589,262 | B1 | 7/2003 | Honebrink et al. |
| 6,623,460 | B1 | 9/2003 | Heck |
| 6,641,564 | B1 | 11/2003 | Kraus |
| 6,712,789 | B1 | 3/2004 | Lange et al. |
| 6,712,791 | B2 | 3/2004 | Lui et al. |
| 6,764,464 | B2 | 7/2004 | McGuckin, Jr. et al. |
| 6,796,991 | B2 | 9/2004 | Nardeo |
| 6,808,509 | B1 | 10/2004 | Davey |
| 6,827,710 | B1 | 12/2004 | Mooney et al. |
| 6,837,873 | B1 | 1/2005 | Polley et al. |
| 6,966,896 | B2 | 11/2005 | Kurth et al. |
| 7,008,404 | B2 | 3/2006 | Nakajima |
| 7,101,353 | B2 | 9/2006 | Lui et al. |
| 7,192,433 | B2 | 3/2007 | Osypka et al. |
| 7,422,571 | B2 | 9/2008 | Schweikert et al. |
| 2001/0049499 | A1 | 12/2001 | Lui et al. |
| 2003/0050604 | A1* | 3/2003 | Lui et al. ............... 604/167.06 |
| 2003/0085373 | A1 | 5/2003 | Dehdashtian |
| 2003/0088264 | A1 | 5/2003 | Spohn et al. |
| 2004/0059296 | A1* | 3/2004 | Godfrey ................ 604/164.05 |
| 2004/0102738 | A1 | 5/2004 | Dikeman et al. |
| 2004/0143219 | A1 | 7/2004 | Lee et al. |
| 2004/0193119 | A1 | 9/2004 | Canaud et al. |
| 2004/0267202 | A1 | 12/2004 | Potter |
| 2005/0010238 | A1 | 1/2005 | Potter et al. |
| 2005/0043684 | A1 | 2/2005 | Basta et al. |
| 2005/0049628 | A1 | 3/2005 | Schweikert et al. |
| 2005/0113757 | A1 | 5/2005 | McFarlane |
| 2005/0267487 | A1 | 12/2005 | Christensen et al. |
| 2006/0149293 | A1 | 7/2006 | King et al. |
| 2007/0106262 | A1 | 5/2007 | Becker et al. |
| 2007/0123825 | A1 | 5/2007 | King et al. |
| 2009/0143739 | A1 | 6/2009 | Nardeo et al. |
| 2009/0234290 | A1 | 9/2009 | Fisher et al. |

FOREIGN PATENT DOCUMENTS

| | | |
|---|---|---|
| EP | 1634615 A1 | 3/2006 |
| WO | WO9714456 A1 | 4/1997 |
| WO | 99/45996 | 9/1999 |
| WO | WO03002182 A1 | 1/2003 |
| WO | WO2005013807 A2 | 2/2005 |

OTHER PUBLICATIONS

Written Opinion (corrected), dated Mar. 26, 2009; PCT/US2008/067631 (9 pages).

International Preliminary Report on Patentability dated Jun. 18, 2010; PCT Application No. PCT/US08/067631 (12 pages).

Office Action dated Oct. 5, 2009; U.S. Appl. No. 12/283,933 (18 pages).

Office Action dated Mar. 23, 2010; U.S. Appl. No. 12/283,933 (7 pages).

Office Action dated Sep. 9, 2009; U.S. Appl. No. 12/144,297 (23 pages).

International Preliminary Report dated Sep. 23, 2010; PCT/US2009/036486 (9 pages).

* cited by examiner

HEMOSTASIS VALVE

CROSS-REFERENCE TO RELATED APPLICATIONS

The present application claims priority from U.S. patent application Ser. No. 12/144,297 filed Jun. 23, 2008, which claims priority from U.S. Provisional Patent Application Ser. No. 60/936,795 filed Jun. 22, 2007.

FIELD OF THE INVENTION

The invention relates to medical devices and more particularly to devices for use in insertion or implantation of catheters and the like into the vasculature of patients.

BACKGROUND OF THE INVENTION

Catheters are used in numerous medical procedures. In particular, catheters are used for the introduction or removal of fluids from various venous regions and vessels throughout the body, such as for hemodialysis. The procedure by which these catheters are introduced to the body is delicate and complex. One particularly intricate challenge to catheterization is enlarging a hole in the flesh and vessel to be catheterized while minimizing blood loss and trauma to the patient. Generally, to insert any catheter in a blood vessel, the vessel is identified by aspiration with a long hollow needle in accordance with the Seldinger technique. When blood enters a syringe attached to the needle, indicating that the vessel has been found, a thin guide wire is then introduced, typically through the syringe needle or other introducer device, into the interior of the vessel. The introducer device is then removed, leaving the guide wire within the vessel. The guide wire projects beyond the surface of the skin.

At this point, several options are available to a physician for catheter placement. The simplest option is to pass a catheter into the vessel directly over the guide wire. The guide wire is then removed. However, use of this technique is only possible in cases where the catheter is of a relatively small diameter, made of a stiff material and not significantly larger than the guide wire. If, however, the catheter is of a relatively large diameter and/or not made of a soft material, one preferable method of inserting the catheter into the vessel is through an introducer sheath. The introducer sheath is simply a large, stiff, thin-walled tube, which serves as a temporary conduit for the catheter that is being placed. The sheath is positioned by placing a dilator, which has a hollow passageway along its longitudinal axis, inside of the sheath and passing both the dilator and the sheath together into the vessel over the guide wire. The dilator expands the opening in the blood vessel to allow for catheter insertion into the vessel. The guide wire and dilator are then removed, leaving the thin-walled sheath in place. The catheter is then inserted into the vessel through the sheath.

In a setting where a catheter with a hub or other attachment at the proximal end of the catheter has a feature which is larger than that of the inner diameter of the sheath, it is necessary to have a tear-away sheath that can be split away from the catheter as the sheath is being removed from the patient. An example of such a tear-away, or splittable or peelable, sheath, with dilator is set forth in U.S. Pat. No. 6,796,991, which is depicted herein in PRIOR ART FIGS. 1 and 2 hereof. By splitting the sheath along its longitudinal axis as the sheath is being removed from the patient, the inserting physician will be able to pull out the sheath in such a way that the portion removed from the patient is split, thereby not interfering with any encumbrances on the catheter. Generally, tear away sheaths are manufactured in a way that aids in the tearing of the sheath at two opposing points on the circumference of the sheath, thereby splitting the sheath into two halves separated longitudinally through the center of the sheath.

A sheath is generally constructed with a hub at its proximal end. This hub serves as a handle, a mating point for a dilator, and a flat surface to aid in the prevention of blood loss or contamination. When a sheath needs to be split apart in order to be successfully withdrawn from the body while leaving the catheter in place, the hub will also have to be split apart in order to clear the catheter. Preferably, the hub will split along the same lines as the sheath. To accomplish this, the hub must be designed with reveals or other weaknesses along two longitudinal lines aligned with the weaknesses in the sheath. Some previous examples of these weaknesses are tabs or webs which connect two halves of the hub, or recesses in the material comprising the hub. The weaknesses in the hub will help the inserting physician to break apart the hub in line with the tear seams on the sheath.

Another important facet of the hub is a set of tabs or wings that protrude from the center. These tabs not only help the inserting physician to align, insert and withdraw the sheath, but also to pull the sheath so that the sheath can be removed from around a catheter while still leaving the catheter in place. There are a number of different tab configurations, but it is important to have one which allows for easy maneuverability, control, and leverage. One design includes a hub wherein the tabs protrude from the hub perpendicular to a plane which includes the tear seams in the sheath and the longitudinal axis of the sheath. In this design, the tabs are diametrically opposed from each other and are spaced in such a way that when the tabs are grasped and pulled apart from each other, the sheath and its hub will split down the middle. Another desirable feature of the tabs is that the tabs provide leverage for breaking apart the hub in a manner that does not cause trauma to the incision in the body.

During insertion, especially in the time between the removal of the dilator from the sheath and the insertion of the catheter through the sheath, it is possible for blood loss through the sheath, or the introduction of contaminants or air through the sheath and into the vessel. For this reason, it is desirable that measures be taken to prevent blood, air or contaminants from traveling through the sheath. In the past, inserting physicians have simply held their thumb over the opening in the proximal end of the sheath; however, a more permanent and reliable means for preventing blood, air or contaminants from traveling through the sheath is desirable. It is therefore desirable for the hub to include a valve located in the sheath. Such a valve would facilitate the insertion of objects such as a catheter, dilator or syringe through the sheath while restricting blood loss and reducing the chance of contaminants entering the patient's bloodstream when the sheath is not engaged with a dilator or a catheter.

In the case where a sheath does not have a small diameter or a narrow point, the dilator is often used to aid in the insertion of the sheath. The dilator has a long tubular section, the outside diameter of which is slightly smaller than the inside diameter of the sheath. The dilator also has a pointed tip on its distal end and a hollow center, which runs along the entire length of the dilator. The dilator is inserted into the body with the guidewire running through its center, thereby allowing the tip of the dilator to follow the guidewire to the place that is to be catheterized. On its proximal end, the dilator may have a hub. Like the hub of the sheath, this hub can also serve a number of purposes, such as providing a stable handle to aid in guiding the dilator into the vein, and as a mechanism which can mate with the sheath hub to form a locked connection.

In PRIOR ART FIGS. 1 and 2, a releasably locking dilator and sheath assembly and methods for releasing the dilator from the sheath and longitudinally splitting the sheath are provided. The assembly includes a dilator having a dilator hub and a sheath having a sheath hub. The sheath hub has a valve and two opposing winged tabs, each tab having a perpendicular portion and an angled portion as well as a female threaded portion. The dilator hub has a male threaded portion designed to engage the female threaded portion of the sheath hub. The dilator is released from the sheath by rotating the dilator 90° in relation to the sheath and pulling the dilator out of the sheath. The sheath is longitudinally split by creating a coupling moment on each of the winged tabs thereby forcing the sheath and the sheath hub to split longitudinally. With the sheath, the valve and the sheath hub split longitudinally, the sheath is removed from around a catheter while leaving the catheter in place.

It is desired to provide a hemostasis valve for a splittable sheath, and to provide a sheath assembly with hemostasis valve and sheath hub for use therewith, that are splittable for facilitating removal of the sheath from about an inserted catheter.

BRIEF SUMMARY OF THE INVENTION

The present invention is a tearaway sheath assembly having a splittable sheath tube and a splittable hub affixed thereto, with the hub being at the proximal end of the sheath assembly, the sheath tube extending to a smaller diameter distal sheath end, a passageway extending through the assembly from the proximal end to the distal end and defining a longitudinal axis therethrough. The sheath tube includes opposed frangible seams therealong to facilitate peeling or splitting during the tearaway procedure.

The assembly of the present invention also includes a splittable hemostasis valve seal contained and affixed within the hub. The hub comprises two opposing sections joined to each other at frangible joints or webs until intentionally split apart, so that the hub remains an integral one-piece unit until split by the practitioner after insertion of the catheter into a patient's vasculature has been accomplished, with a grippable wing joined to each hub section for handling and for initiating splitting in a manner known in the art. The hub also provides distinct opposing gaps between the two opposing sections that are joined at frangible sections within the gaps, where the gaps are aligned with opposed frangible seams of the sheath tube, so that upon splitting of the hub by the practitioner, the sheath tube also splits apart as the tearaway procedure continues. A valve seal contained within the proximal end of the hub is also splittable when the hub is intentionally split but otherwise remains intact to provide hemostasis; the valve is selectively openable prior to splitting to permit insertion therethrough of a dilator and later of a catheter forming a seal therewith and therearound, but otherwise remains closed to prevent blood effusion.

In a preferred embodiment, the splittable valve is of a duckbill type and has an elongate structure with distal and proximal ends, the duckbill structure being disposed at its distal end, and comprising a pair of angled converging side walls, and includes a slit partially across the converging ends of the side walls and preferably through the axial center of the valve. Proximally of the slit distal end, the valve transitions to a cylindrical or tubular structure at its proximal end. Preferably, a cap is securable to the proximal end of the sheath hub to secure the valve in a tubular proximal end portion of the hub; and, further, the cap is preferably comprised of two separate parts separated along a radial aligned with the gaps of the hub and the seams of the sheath tube with each half affixed to a respective section of the hub at the proximal end, to prevent inhibiting the splitting procedure by the practitioner.

The hub of the sheath assembly of the present invention includes a valve-containing proximal portion adjacent its proximal end, and include a distal portion that is affixed to a proximal end of the sheath tube. The two opposing sections of the hub have opposing gaps spacing them apart, but have frangible sections within the gaps to maintain the two opposing hub sections joined to each other until intentionally split. The opposing gaps are aligned with the frangible seams of the sheath tube. Preferably, the frangible sections are located at a transition portion axially between the proximal hub portion and the distal hub portion and at the distal end of the valve-containing proximal portion where the hub diameter narrows, and comprise thin web sections.

BRIEF DESCRIPTION OF THE DRAWINGS

The accompanying drawings, which are incorporated herein and constitute part of this specification, illustrate the presently preferred embodiments of the invention, and, together with the general description given above and the detailed description given below, serve to explain the features of the invention. In the drawings.

DETAILED DESCRIPTION OF THE INVENTION

Figure 1:
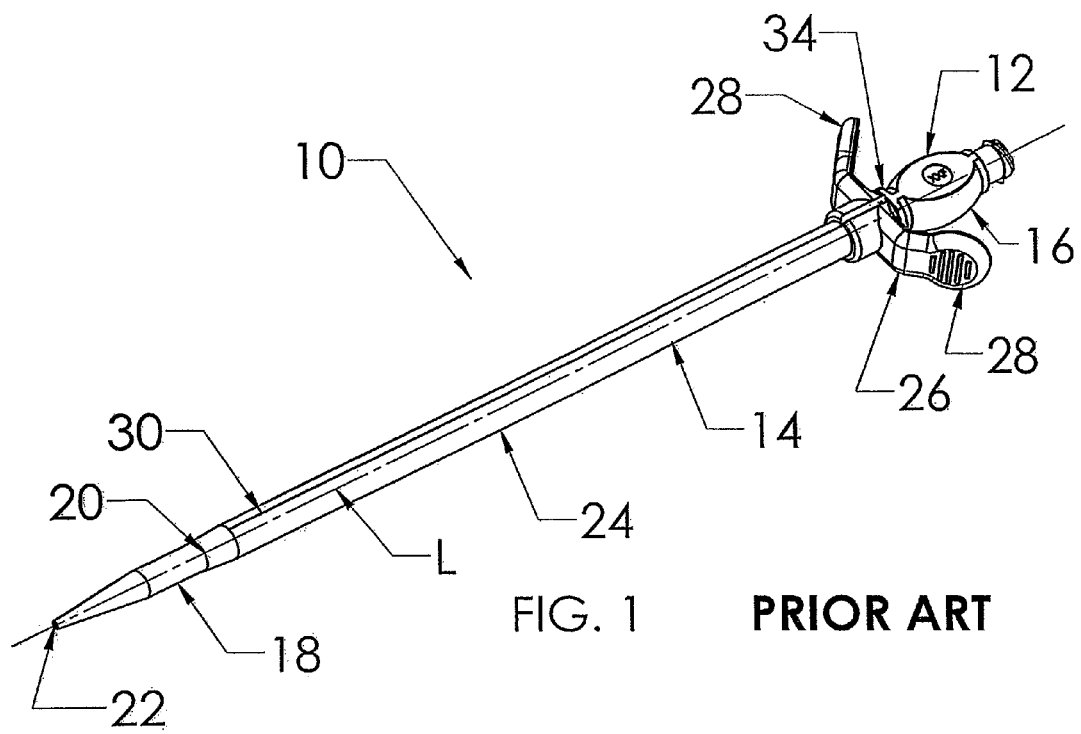
FIGS. 1 and 2 are isometric views of a PRIOR ART sheath/dilator assembly, and the sheath of the assembly shown with the dilator removed.

In the drawings, like numerals indicate like elements throughout. Certain terminology is used herein for convenience only and is not to be taken as a limitation on the present invention. The terms "distal" and "proximal" refer, respectively, to directions closer to and away from the patient. The terminology includes the words specifically mentioned, derivatives thereof and words of similar import. The embodiments illustrated below are not intended to be exhaustive or to limit the invention to the precise form disclosed. These embodiments are chosen and described to best explain the principle of the invention and its application and practical use and to enable others skilled in the art to best utilize the invention.

Figure 2:
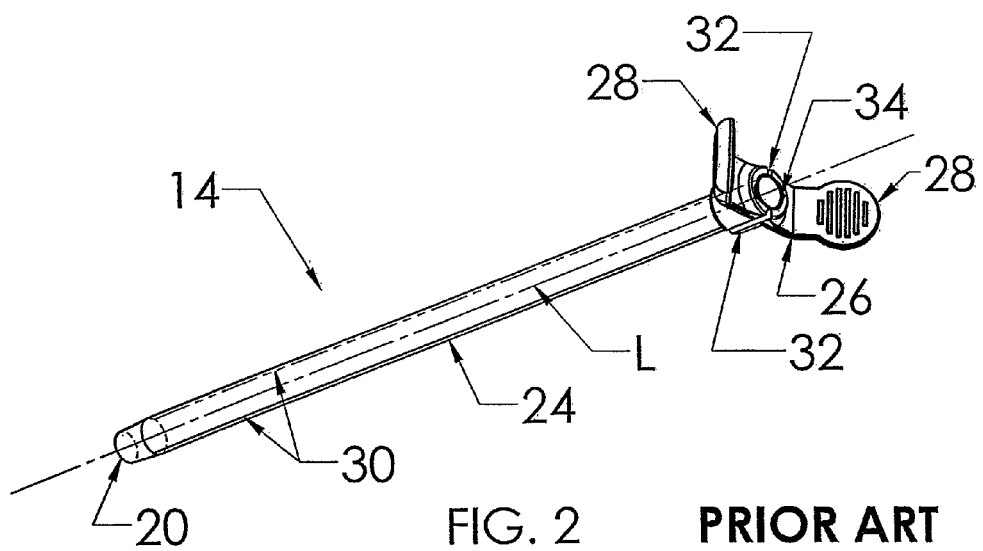

In PRIOR ART FIGS. 1 and 2, a sheath assembly 10 is shown comprising a dilator 12 and a sheath 14, and having a longitudinal axis "L". Dilator 12 has a dilator hub 16 at its proximal end, and its distal end portion 18 extends beyond the distal end 20 of sheath 14 to a distal tip 22. Sheath 14 includes a sheath tube 24 and a sheath hub 26 at the proximal end of the sheath tube, and is seen in FIG. 2 with the dilator removed. Sheath hub 26 is seen to have grippable wings 28 to facilitate the initiation of splitting by the practitioner to peel away the sheath from an inserted catheter (not shown). To facilitate splitting of the sheath 14 from around the catheter, the sheath tube has a pair of opposed frangible seams 30, and sheath hub 26 includes frangible webs along opposed gaps 32 that are aligned with seams 30. The proximal end 34 of sheath 14 includes a threaded locking arrangement for locking with the dilator hub 12 prior to removal of the dilator.

Figure 3:
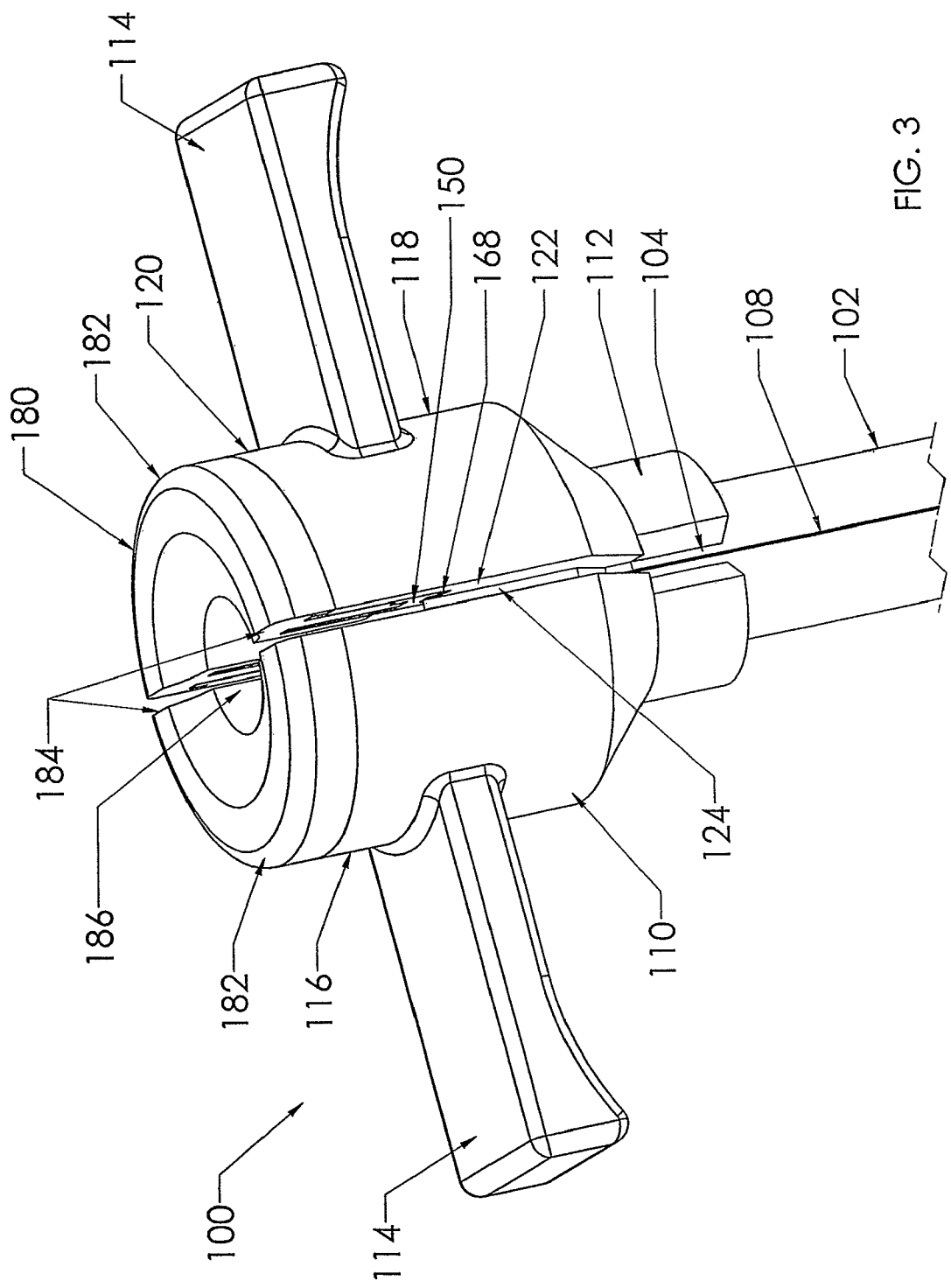
FIG. 3 is an enlarged isometric view of the tearaway sheath assembly of the present invention, showing the sheath hub and valve cap at the proximal end of the sheath tube and the hub's gaps aligned with seams of the sheath tube.

Sheath assembly 100 of the present invention is illustrated in FIGS. 3 to 9. The sheath assembly includes a sheath tube 102 with a proximal end portion 104 and extending to a distal end, with a passageway 106 (FIG. 4) extending therebetween defining a longitudinal axis. The sheath tube 102 includes a pair of opposed seams or frangible sections 108 that define weaknesses along which the sheath tube is easily split by the practitioner after insertion of the catheter's distal portion into the vasculature of a patient (not shown). Referring primarily first to FIG. 3, a sheath hub 110 is affixed to the proximal end portion 104 of the sheath tube at the distal end portion 112 of the hub. A pair of wings or tabs 114 extend from respective opposed sections 116,118 of hub 110, for gripping by the practitioner for initiating the splitting of the sheath assembly for tearing it away from the catheter, by their being pried toward the sheath distal end such that the splitting of the hub begins at its proximal end 120 and separating hub sections 116,118 completely from each other along a pair of opposed gaps 122. Also seen in FIG. 3 is a portion of a frangible section 124 disposed along the inside edge of gap 122; the frangible section or webs on both sides join together the two hub sections 116,118.

Figure 4:
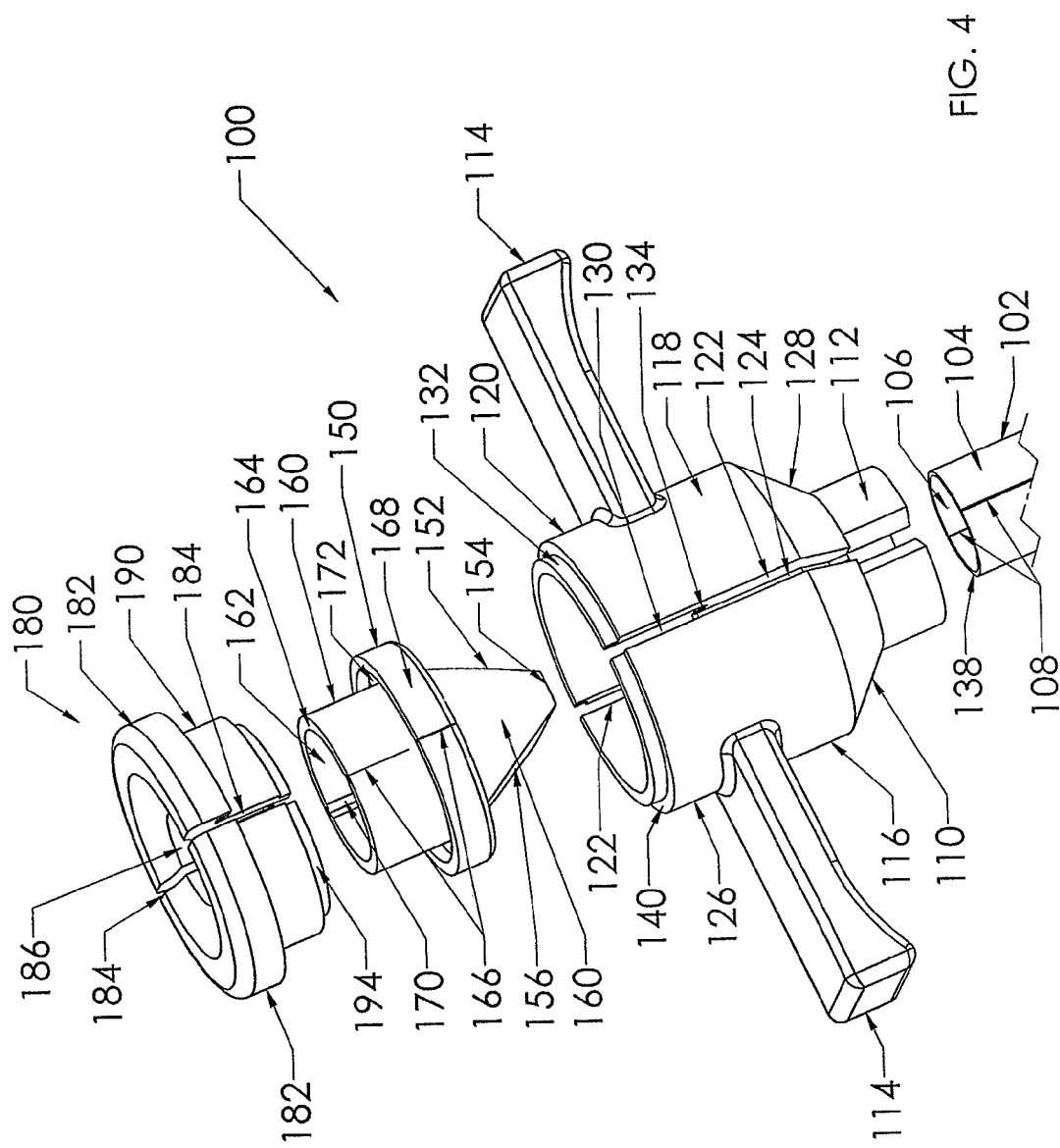
FIG. 4 is an exploded view of the assembly of FIG. 3 and also showing the splittable valve.

Now referring to FIG. 4, hub 110 is exploded from sheath tube 102; splittable valve 150 is exploded from hub 110; and the two halves 182 of cap 180 are exploded from hub 110 and valve 150. Hub 110 includes a large diameter cylindrical portion 126 extending to its proximal end, and a frustoconical transition section 128 joins cylindrical portion 126 to small diameter distal end portion 112. Large diameter cylindrical portion 126 defines therein a large valve-receiving cavity 130. Seen projecting proximally from cylindrical portion 126 is a seating flange 132 associated with seating of the two halves of cap 180, and within gap 122 can be seen a seating flange 134 associated with seating of splittable valve 150.

Splittable valve seal 150 will now be described with reference to FIGS. 4 and 5. Splittable valve seal 150 is of the duckbill type, so-called because its distal end portion 152 is shaped like a duck's bill, and extends to a transverse distal end wall 154. Distal end portion 152 has two converging side walls 156 extending to distal end wall 154, and a slit 158 is seen formed in distal end wall 154 extending mostly but preferably not completely thereacross (see FIG. 9). Cylindrical wall 160 joins together the lateral ends of side walls 156 and defines a large central cavity 162 extending between distal end wall 154 and proximal end 164 of valve 150. Seen best in FIG. 4, slits 166 of limited axial length are cut into side wall 160 and in seating flange 168, to facilitate splitting of the valve. Furthermore, within large central cavity can be seen V-grooves 170 formed into the cylindrical wall 160 that are aligned with and communicate with the slits 166, and are also aligned with gaps 122 of hub 110 and seams 108 of sheath tube 102 in the completed assembly. Seating flange 168 is T-shaped in cross-section, forming distal and proximal seating recesses 172,174, seen best in FIGS. 5 and 6.

Cap 180 preferably comprises two completely separate but identical halves 182, for securing valve 150 within valve-receiving cavity 130 of hub 110, and are bonded or fused to the hub. Cap halves 182, when affixed in place to the proximal end of the hub, are separated by gaps 184 aligned with gaps 122 of hub 110 and seams 108 of sheath tube 102 and V-grooves 170 and slits 166 of valve 150. Cap 180 defines a passageway 186 extending therethrough from a beveled lead-in at the cap's proximal end, with passageway 186 sufficiently large in inner diameter for a dilator and a catheter to be movably inserted therethrough. Cap 180 includes an outer flange at the proximal end defining an outer seating recess 188, within which is received flange 132 of hub 110. An outer cylindrical wall 190 extends distally to an end portion 192 that is associated with proximal seating recess 172 of valve 150. An inner cylindrical wall 194 along passageway 186 is spaced inwardly from outer cylindrical wall 190 to define a deep seating recess 196 associated with the proximal end portion of cylindrical wall 160 of valve 150.

Figure 5:
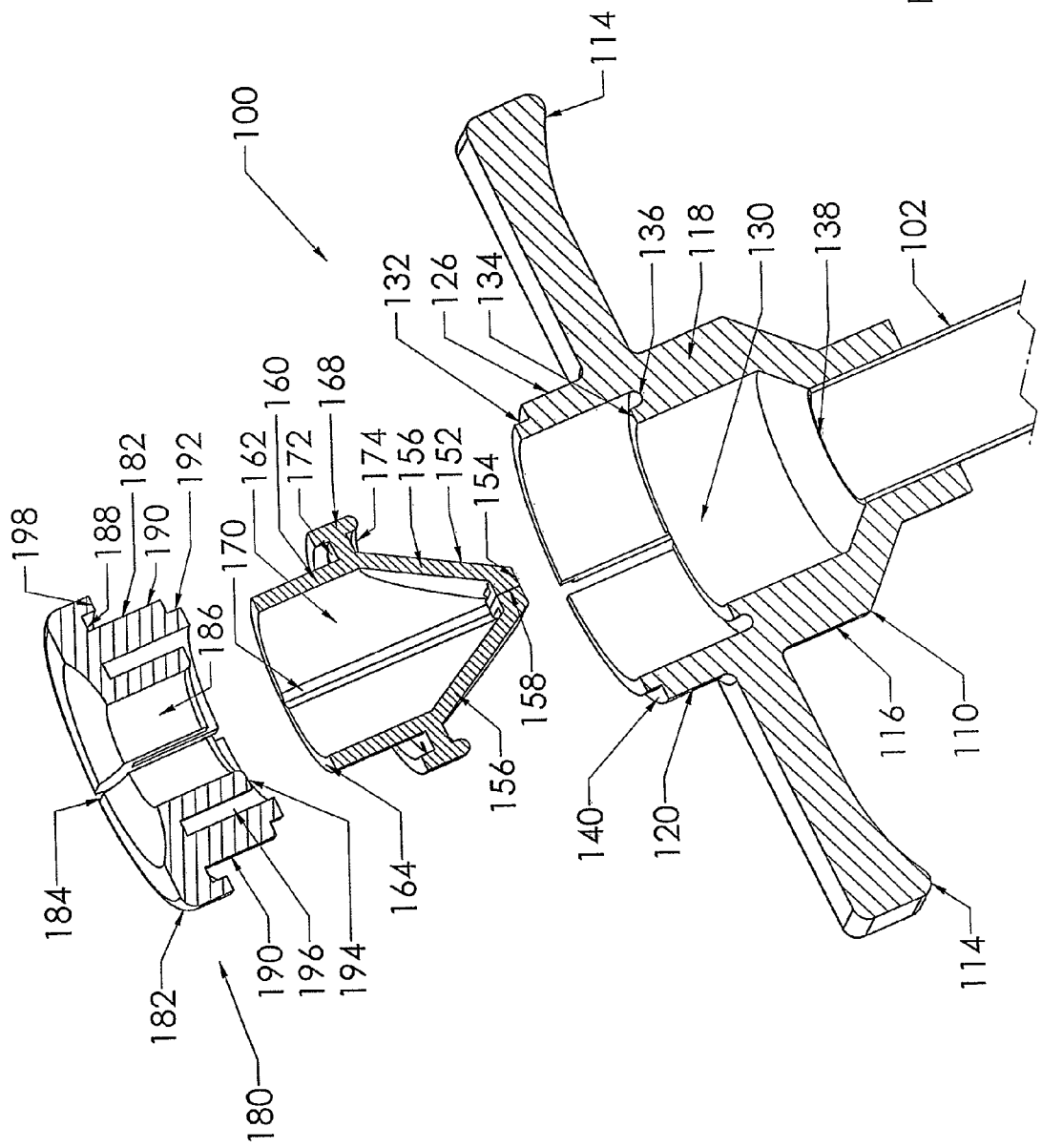
FIG. 5 is a cross-section view of the exploded sheath assembly of FIG. 4.
Figure 6:
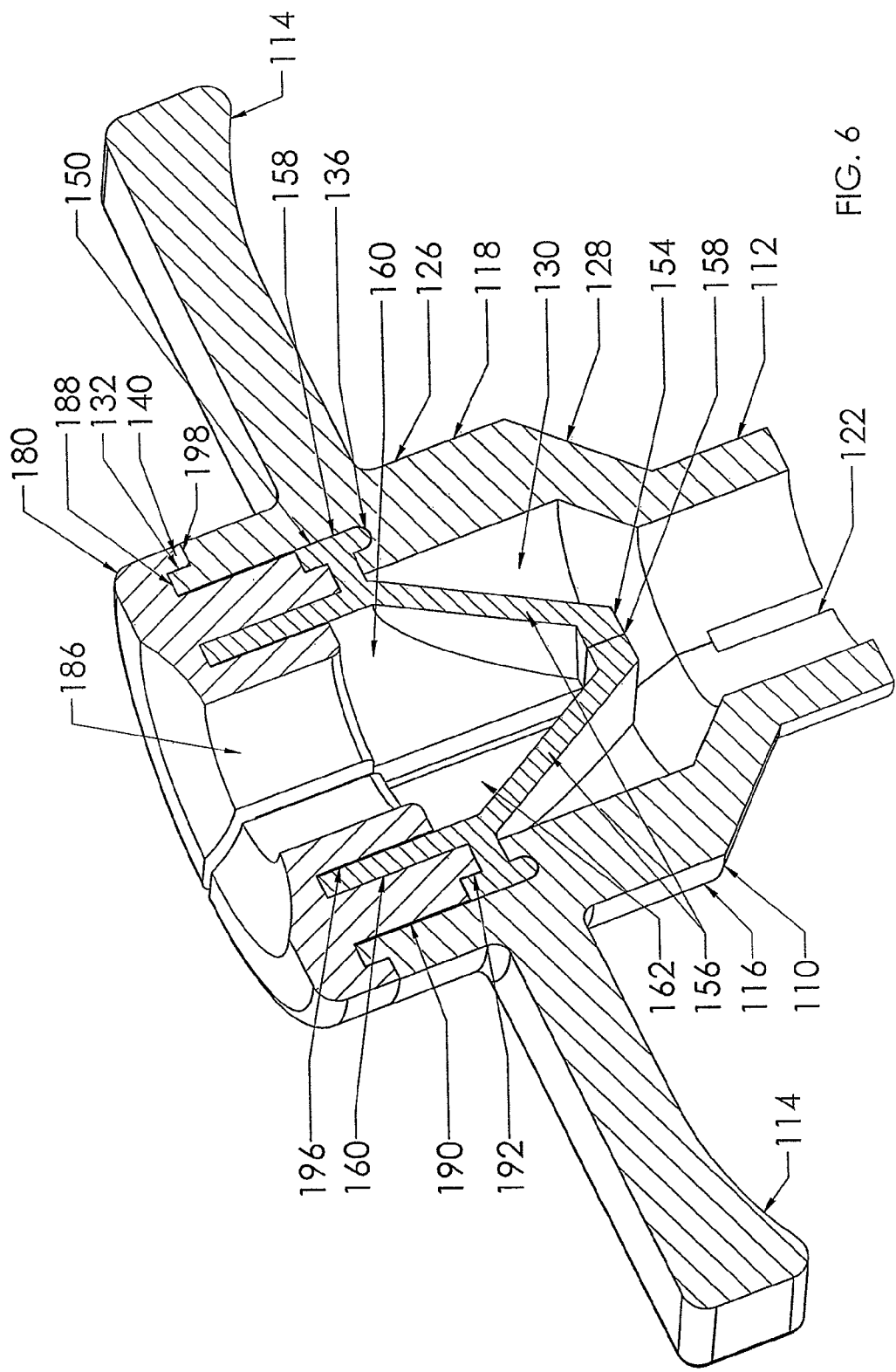
FIG. 6 is a cross-section view of the hub, valve and cap of FIG. 4, assembled.

The interrelationship of the various associated portions of the hub, valve and cap is best explained with respect to FIGS. 5 and 6 for an understanding of assembling them together. Valve 150 is seated within large valve-receiving cavity 130 of hub 110. Distal seating recess 174 of flange 168 is disposed or seated within seating groove 136 defined outwardly of seating flange 134 of hub 110. Proximal seating recess 172 of valve 150 is facing proximally for receipt thereinto of end portion 192 of outer cylindrical wall 190 of cap 180 (see FIG. 4). The proximal end portion of cylindrical wall 160 of valve 150 is associated with deep seating recess 196 of cap 180 between its inner and outer cylindrical walls 194,190. FIG. 5 also shows that the proximal end 138 of sheath 102 extends to the distal end of the valve-receiving cavity 130 of hub 110 to maximize the bonded surface area between the proximal end portion of the sheath and the distal end portion 112 of the hub.

At the proximal end 120 of hub 110, seating flange 132 projects proximally to be received into outer seating recess 188 of cap 180. Bonding or fusing of cap 180 to hub 110 joins the facing surfaces of seating flange 132, outer seating recess 188, the outside surface of outer cylindrical wall 190 and the inside surface of cylindrical wall 126 of hub 110, and proximal ledge 140 around seating flange 132 and the distal face 198 of the outer flange of the cap. Cap halves 182 are affixed to hub 110 in a manner that compresses the seating flange 168 of valve 150 and secures it in place while establishing a seal between the valve and both the cap halves and the hub.

Figure 7:
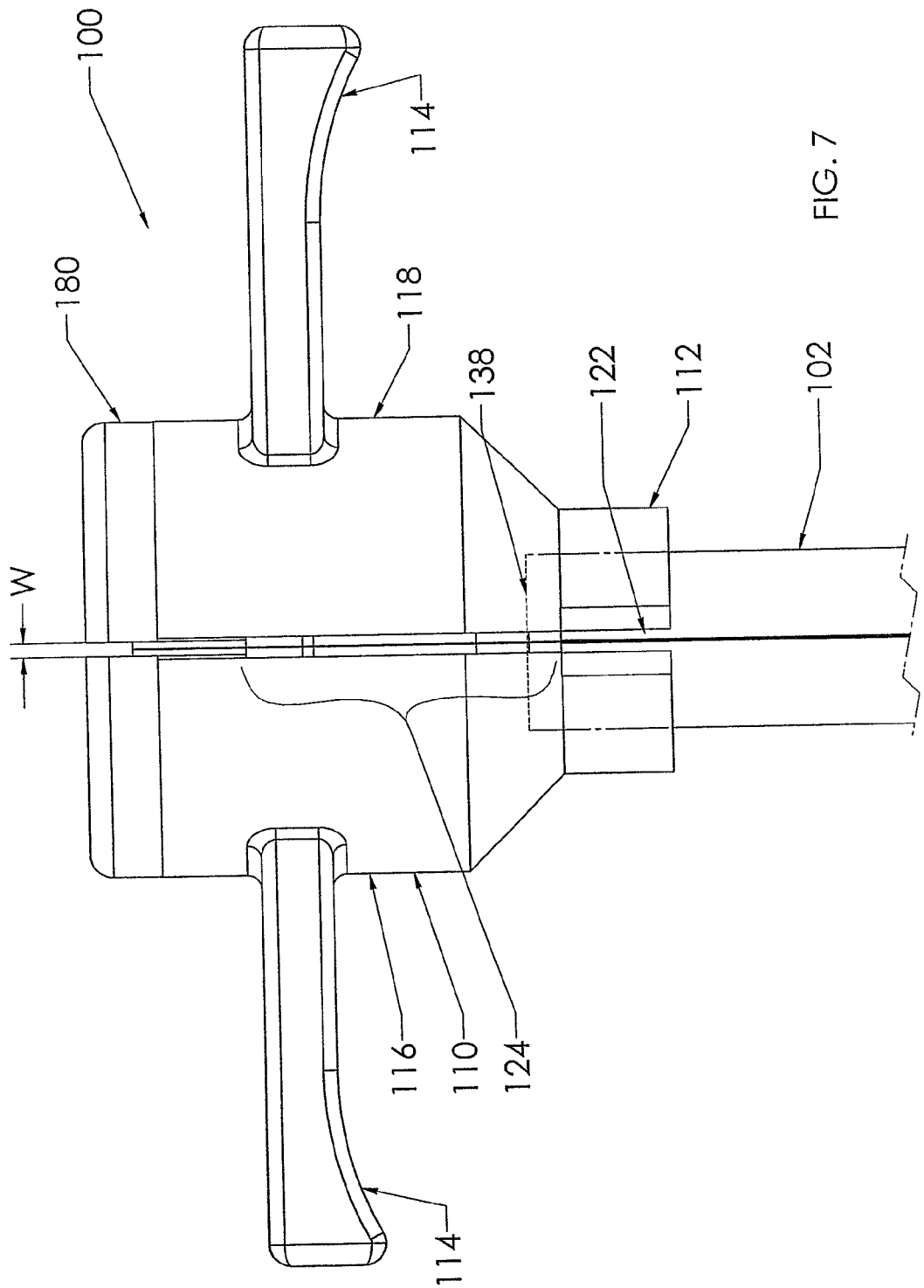
FIG. 7 is an elevation view of the sheath assembly proximal end of FIG. 3 peering directly into the gap of the hub showing the location of the hub frangible webs.
Figure 8:
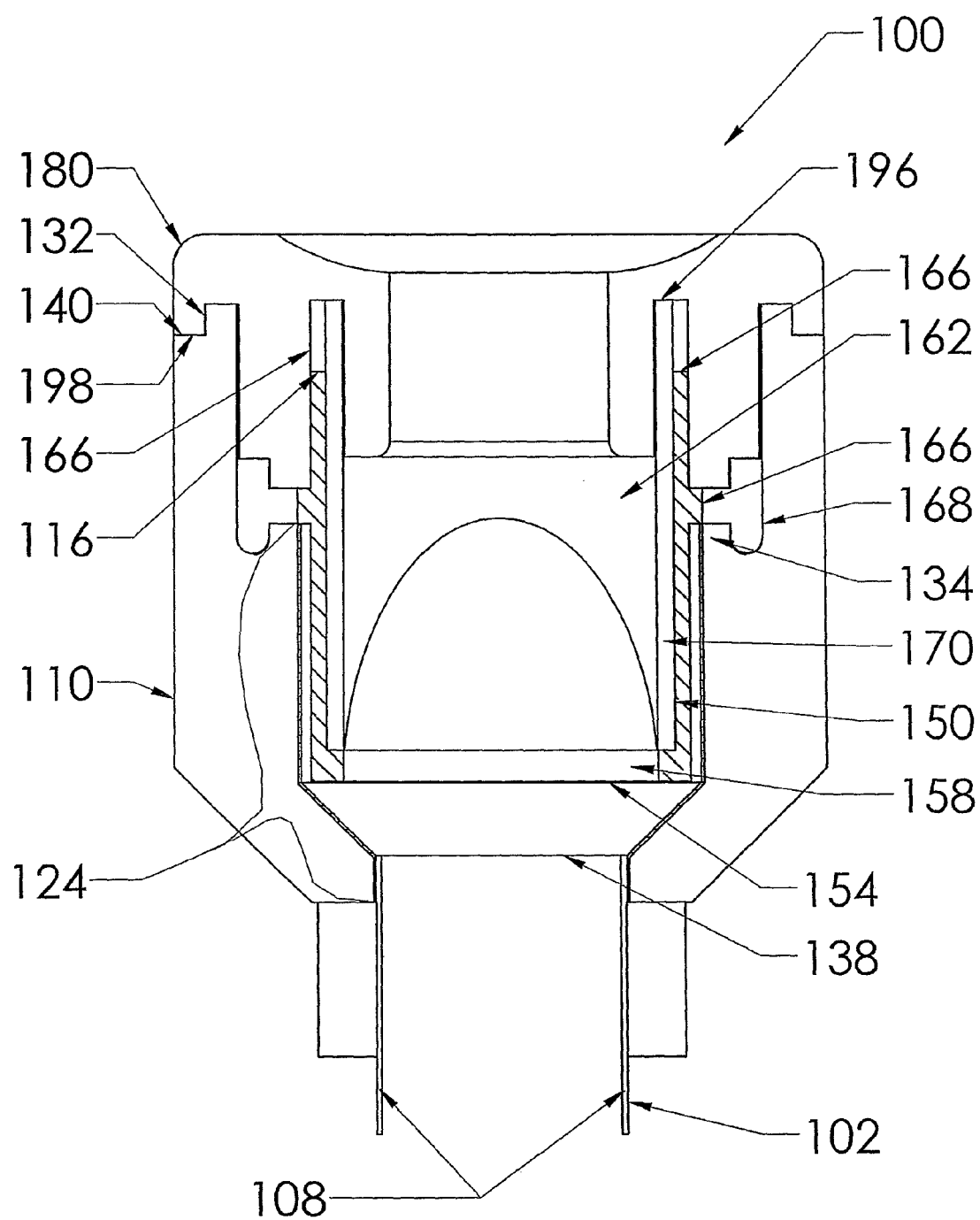
FIG. 8 is a cross-sectional front view of the assembly of FIG. 7 rotated about 90 degrees from that of FIG. 7, showing the frangible web joining the two hub sections.
Figure 9:
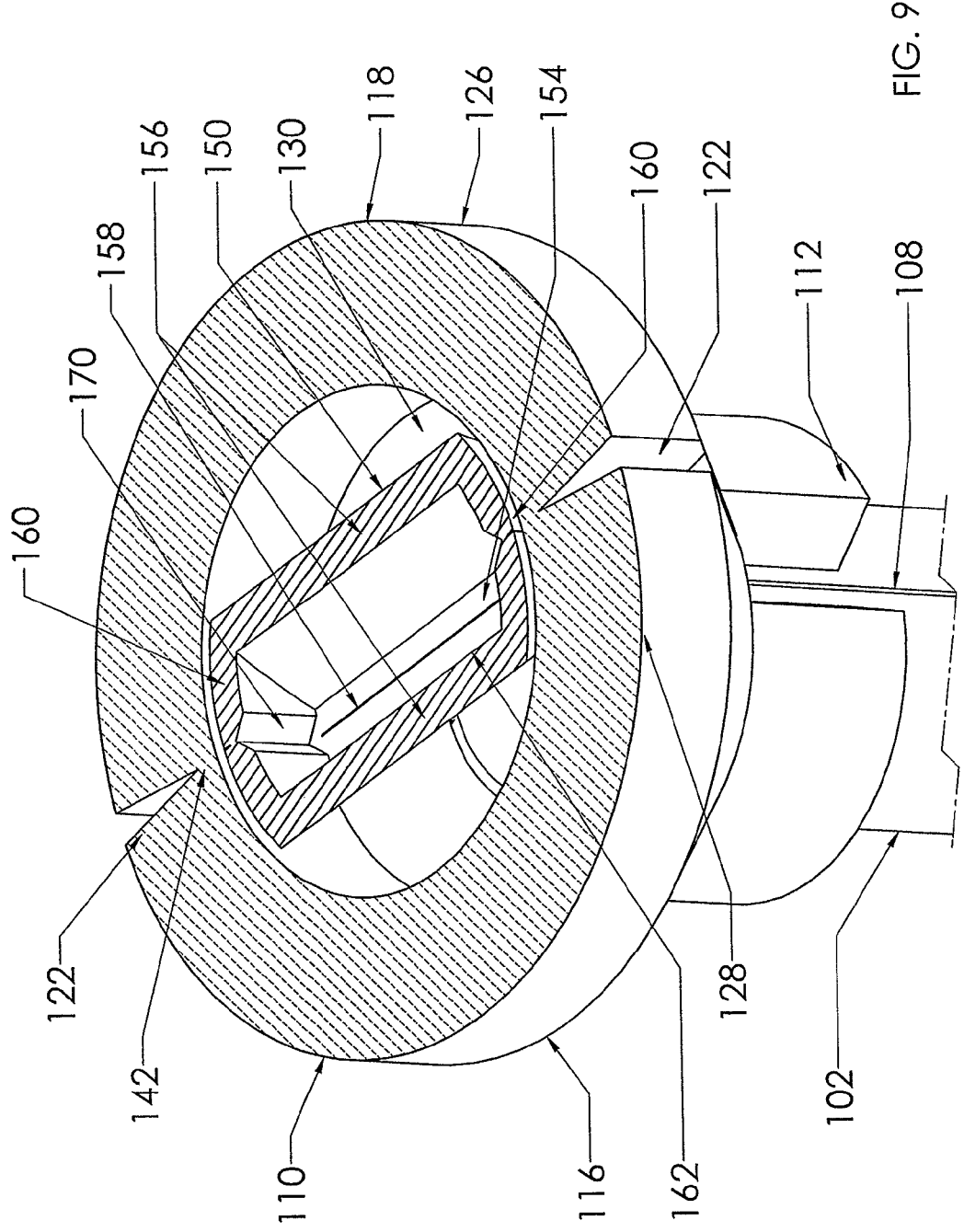
FIG. 9 is a transverse cross-section of the sheath assembly taken just proximally of the distal end of the splittable valve of the present invention.

FIGS. 7 to 9 give a better understanding of frangible sections or webs 124 of hub 110 that join hub sections 116,118. The webs are formed along the inside surface of valve-receiving cavity 130 (FIG. 6) of the hub and are very thin. Preferably, they extend along the intermediate or frustoconical portion 128 of the hub and partially along the cylindrical wall 130, extending to and along seating flange 134. With reference to FIG. 9, it is preferred that, mainly for manufacturing reasons, the gaps 122 of hub 110 extend radially inwardly from hub outer surfaces to inner gap end portions 142 that are V-shaped converging at the frangible webs 124, in order for the mold inserts to remain relatively thick, robust and durable over many molding cycles and also to carefully control the thickness of the frangible webs. The webs may have a thickness, for example, of about 0.002 in (0.0508 mm), and the width W of the gaps 122 at the outer surfaces can be, for example, about 0.050 in (1.270 mm). Similarly, as seen in FIG. 9, frangible sections 170 of the splittable valve 150 may be V-shaped in cross-section, but extending from the inside surface toward the outside surface, preferably about one-half of the thickness, of the cylindrical wall 160.

It can be seen in FIG. 9 that the distal end wall 154 of the valve would be abutted by a proximal end of a guide wire (not shown) during initial placement of the sheath assembly over the guide wire after the guide wire is placed in the vasculature, later by the dilator distal tip inserted through the hub and valve and later by the catheter distal tip, with the slit 158 permitting the diverging side walls to deform as the slit is opened in response to guide wire, dilator or catheter insertion, with the valve maintaining engagement with the outer surfaces of the guide wire, dilator or catheter as it passes therethrough; and the slit will also close against the guide wire upon withdrawal of the dilator from the sheath assembly, forming a hemostasis seal and preventing effusion of blood. The valve may be made of silicone. The hub and the cap may be made of polyethylene or polypropylene. The sheath tube could be made of polyethylene or polytetrafluoroethylene.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

The invention claimed is:

1. A hemostasis valve seal for a tearaway sheath assembly, comprising:
    a valve seal body extending from a proximal valve end to a distal valve end and defining an internal cavity extending from the proximal valve end toward the distal valve end, the proximal valve end includes a cylindrical wall defining a generally open end and tapered side walls extend from the cylindrical wall to the valve distal end which is generally closed except for a transverse slit through the distal valve end; and
    a pair of opposed frangible webs defined to extend axially along the valve seat body aligned with the transverse slit in a given plane, each frangible web includes a V-shaped groove extending along an inside surface of the valve seal body, each V-shaped groove tapering from the inside surface to a groove bottom which is spaced from an outside surface of the valve seal body.

2. The hemostasis valve seal of claim 1 wherein a distal end wall extends between the side walls at the distal end and the transverse slit is defined through the distal end wall.

3. The hemostasis valve seal of claim 2 wherein the transverse slit has opposed slit ends and each slit end is spaced from a respective groove bottom.

4. The hemostasis valve seal of claim 1, wherein each groove bottom is positioned approximately halfway between the inside surface of the valve seal body and an outside surface of the valve seal body.

5. The hemostasis valve seal of claim 1 wherein axial slits are defined into an outer surface of the valve seal body in the given plane.

6. The hemostasis valve seal of claim 5 wherein the axial slits extend adjacent the proximal valve end of the valve seal body.

7. The hemostasis valve seal of claim 1 wherein an annular seating flange extends radially outwardly from the valve seal body.

8. The hemostasis valve seal of claim 7 wherein axial slits are defined completely through the annular seating flange on opposite sides of the flange in the given plane.

* * * * *